United States Patent [19]

Akemi et al.

[11] Patent Number: 5,204,109

[45] Date of Patent: Apr. 20, 1993

[54] PERCUTANEOUS GEL PREPARATION

[75] Inventors: Hitoshi Akemi; Saburo Otsuka; Takashi Kinoshita; Yoshifumi Hosaka; Yoshihisa Nakano, all of Osaka, Japan

[73] Assignees: Nitto Denko Corporation, Osaka; Toa Eiyo Ltd., Tokyo, both of Japan

[21] Appl. No.: 855,493

[22] Filed: Mar. 23, 1992

Related U.S. Application Data

[63] Continuation of Ser. No. 635,024, Dec. 28, 1990, abandoned.

[30] Foreign Application Priority Data

Dec. 28, 1989 [JP] Japan ................. 7-344639
Sep. 6, 1990 [JP] Japan ................. 2-237384

[51] Int. Cl.$^5$ .................. A61K 9/70; A61K 31/34; A61L 15/16
[52] U.S. Cl. .................. 424/443; 514/470; 424/446; 424/449
[58] Field of Search ........... 424/487, 443, 446, 449; 514/470

[56] References Cited

U.S. PATENT DOCUMENTS 4,608,249 8/1986 Otsuka .................. 424/28
4,784,856 11/1988 Fukuda et al. .................. 424/448

FOREIGN PATENT DOCUMENTS

| | | |
|---|---|---|
| 0062682 | 10/1982 | European Pat. Off. . |
| 8600814 | 2/1986 | European Pat. Off. . |
| 0181970 | 5/1986 | European Pat. Off. . |
| 8606281 | 11/1986 | European Pat. Off. . |
| 0223524 | 5/1987 | European Pat. Off. . |
| 2421610 | 4/1979 | France . |
| 2497457 | 7/1982 | France . |
| 171913 | 10/1982 | Japan . |
| 105914 | 6/1983 | Japan . |
| 152551 | 8/1985 | Japan . |
| 018717 | 1/1986 | Japan . |
| 034942 | 2/1987 | Japan . |
| 8808310 | 11/1988 | World Int. Prop. O. . |

OTHER PUBLICATIONS

European Search Report.

*Primary Examiner*—Frederick E. Waddell
*Assistant Examiner*—Minna Moezie
*Attorney, Agent, or Firm*—Sughrue, Mion, Zinn, Macpeak & Seas

[57] ABSTRACT

A percutaneous gel preparation is disclosed, which comprises a substrate having one surface thereof a crosslinked gel layer formed by crosslinking a composition comprising the following ingredients (a) to (c), the weight ratio of the ingredient (b) to the ingredient (c) being from 1.0/0.25 to 1.0/2.0:
 (a) isosorbide dinitrate;
 (b) an acrylate polymer; and
 (c) a liquid ingredient compatible with the ingredient (b).

10 Claims, No Drawings

PERCUTANEOUS GEL PREPARATION

This is a continuation of application Ser. No. 07/635,024 filed Dec. 28, 1990, now abandoned.

FIELD OF THE INVENTION

The present invention relates to a percutaneous gel preparation which is to be applied to the surface of the skin so as to continuously administer isosorbide dinitrate to the living body via the skin surface.

BACKGROUND OF THE INVENTION

Recently various percutaneous preparations in the form of a preparation to be applied to the skin (for example, plaster, tape), whereby a drug is administered to the living body via the skin surface, have been developed.

Such a percutaneous preparation to be applied to the skin usually involves an adhesive layer having a relatively large adhesiveness in order to secure the fixation of the preparation on the skin surface. Alternately, the whole preparation is covered with a highly adhesive sheet having a large adhesiveness which secures the fixation of the preparation on the skin.

Although a percutaneous preparation to be applied to the skin should be surely fixed on the skin so as to secure the migration of a drug component into the skin, an excessively large adhesiveness might bring about a pain or the peeling of the horny substance caused by physical stimulation upon the separation of the preparation from the skin surface. Further, serious skin irritation is sometimes observed.

Thus, the adhesiveness to the skin is an important factor in the development of a percutaneous preparation in practice, and the problem of the skin irritation is also an important factor. Therefore, it has been practically required to develop a preparation which scarcely irritates the skin and can be securely fixed onto the skin.

A percutaneous preparation containing isosorbide dinitrate has been already developed as a preparation for percutaneously administering a drug component.

This preparation, which is in the form of a tape comprising isosorbide dinitrate contained in a specific adhesive, exerts a sufficient effect of preventing a fit of, for example, stenocardia. In the case of this preparation comprising isosorbide dinitrate contained in the adhesive, sufficient consideration should be given in the formulation in order to prevent the aforesaid skin irritation. However, although this preparation is good in adhesion to the skin as well as adhesion property against sweat and water, pain is caused upon peeling from the skin after the long time application. Further, the adhesive is less flexible, and therefore this preparation is difficult to sufficiently follow the action of the skin.

SUMMARY OF THE INVENTION

Under these circumstances, the present inventors have conducted extensive studies in order to solve the above problems. As a result, it has been found that a decrease in the cohesive power of the adhesive can be prevented and the stress applied to the skin surface upon the separation of the preparation can be relieved and dispersed so as to achieve well-balanced skin adhesiveness and skin irritativeness by blending an acrylate polymer, which is excellent in the stability and releasing properties for isosorbide dinitrate, with a relatively large amount of a liquid ingredient at a specific ratio and subjecting the thus-obtained composition to crosslinking to thereby give an oily crosslinked gel layer, thus completing the present invention.

An object of the present invention is to provide a percutaneous gel preparation capable of continuously administering isosorbide dinitrate t the living body.

Other objects and effects of the present invention will be apparent from the following description.

The present invention provides a percutaneous gel preparation comprising a substrate having one surface thereof a crosslinked gel layer formed by crosslinking a composition comprising the following ingredients (a) to (c), the weight ratio of the ingredient (b) to the ingredient (c) being from 1.0/0.25 to 1.0/2.0:

(a) isosorbide dinitrate;
(b) an acrylate polymer; and
(c) a liquid ingredient compatible with the ingredient (b).

DETAILED DESCRIPTION OF THE INVENTION

The substrate to be used in the percutaneous gel preparation of the present invention is not particularly limited, but materials, which would never suffer from any decrease in the content of the liquid ingredient or isosorbide dinitrate contained in the crosslinked gel layer caused by the migration toward another surface of the substrate followed by leakage, are preferable. Examples thereof include sole films of polyester, nylon, Saran resins, polyethylene, polypropylene, polyvinyl chloride, ethyleneethyl acrylate copolymer, polytetrafluoroethylene, Surlyn resins and metal foils as well as laminate films comprising these materials. Among these, it is preferred to use a substrate in the form of a laminate film composed of a nonporous sheet comprising one or more materials as cited above and a porous film and to form a crosslinked gel layer on the surface of the porous sheet, to thereby improve the adhesiveness between the substrate and the crosslinked gel layer by the anchoring effect which will be described hereinbelow.

The material of the porous film is not particularly restricted, so long as the anchoring effect to the crosslinked gel layer can be improved. Examples thereof include paper, woven fabric, nonwoven fabric and mechanically perforated sheet. It is particularly preferred to use paper, woven fabric and nonwoven fabric therefor. When the improvement of the anchoring effect and the flexibility of the whole preparation are taken into consideration, the thickness of the porous film is preferably from 10 to 500 $\mu$m, and in the case of a thin preparation such as plaster or tape, it is more preferably from 10 to 200 $\mu$m. When the laminate film composed of the above porous film and the nonporous sheet is used as the substrate, the thickness of the nonporous sheet is preferably from 0.5 to 50 $\mu$m, and more preferably from 1 to 25 $\mu$m.

When woven fabric or nonwoven fabric is used as the porous film, the weight per unit area of the woven or nonwoven fabric is preferably from 5 to 30 $g/m^2$, still preferably from 8 to 20 $g/m^2$, from the viewpoint of the improvement of the anchoring effect.

In the present invention, the crosslinked gel layer to be formed on one face of the aforesaid substrate is a layer of a crosslinked structure obtained by crosslinking a composition comprising isosorbide dinitrate (ingredient (a)), an acrylate polymer (ingredient (b)) and a liquid ingredient compatible with the ingredient (b) (ingredient (c)) and having an appropriate adhesiveness to the skin and an appropriate cohesive power. The adhesiveness is generally from 70 to 250 g/12 mm width in terms of the adhesiveness to a bakelite plate (the determination method therefor will be described in detail hereinafter) and from 20 to 80 g in the probe-tack test.

The acrylate copolymer serves as a main component constituting the crosslinked gel layer together with the liquid ingredient which will be described in detail hereinafter. It sustains a high compatibility with the liquid ingredient and thus shows an excellent adhesiveness to the skin surface as well as an excellent shape retention. In the present invention, it is not preferred to use rubber such as natural or synthetic rubber or a silicone polymer since these materials have a poor compatibility with the liquid ingredient to be used in the present invention or show a considerably low solubility or release of the drug component. In addition, it is difficult to control the amount of functional groups participating in the crosslinking of such a polymer, compared with the acrylate polymer to be used in the present invention, and thus highly reproducible crosslinking can hardly be achieved. These facts indicate that the above-mentioned polymers are unsuitable in the present invention.

As the acrylate polymer (ingredient (b)) to be used in the present invention, a polymer obtained by polymerizing alkyl (meth)acrylates commonly used in the production of an adhesive as the main monomer may be employed. Among these polymers, a copolymer of an alkyl (meth)acrylate with (meth)acrylic acid may be particularly preferable since it may be preferably used together with isosorbide dinitrate. As the alkyl (meth)acrylate, those having an alkyl group carrying 4 or more carbon atoms are preferable. Examples of the alkyl (meth)acrylate include (meth)acrylates having straight-chain or branched alkyl groups, for example, butyl, pentyl, hexyl, heptyl, octyl, nonnyl, decyl, undecyl, dodecyl and tridecyl. Among these, 2-ethylhexyl acrylate, isooctyl acrylate and isononyl acryrate are preferably used. Either one or more of these (meth)acrylates may be used.

The terms "(meth)acrylate", etc. used herein mean "acrylate and/or methacrylate", etc.

Further, the above-mentioned (meth)acrylate(s) is preferably copolymerized with (meth)acrylic acid. The addition of the (meth)acrylic acid, even in a small amount, would improve the cohesive power of the crosslinked gel layer. Furthermore, it exerts a useful effect in the crosslinking reaction as described in detail hereinafter.

The weight ratio of the above-mentioned monomers at the polymerization may be arbitrarily selected depending on the gel properties of the target gel preparation and the release property of the isosorbide dinitrate. The weight ratio of the alkyl (meth)acrylate to the (meth)acrylic acid is preferably (90-99)/(1-10), more preferably (92-97)/(3-8) while the total amount of these comonomers being 100.

The liquid ingredient (ingredient (c)) to be used in the present invention has a high compatibility with the above-mentioned acrylate copolymer (ingredient (b)). The ingredient (c) moderately plasticizes the crosslinked gel layer and thus imparts a flexible texture, to thereby relive a pain or skin irritativeness caused by the skin adhesiveness upon the separation of the crosslinked gel layer from the skin surface. Since the crosslinked gel layer is plasticized thereby, furthermore, the isosorbide dinitrate contained in the crosslinked gel layer can be freely dispersed, thus achieving an improved release property. Therefore, the liquid ingredient may be selected from among materials having a plasticizing effect. A substance which further has an absorption-promoting effect may be selected therefor to thereby improve the percutaneous absorption of the drug component used together.

Examples of the liquid ingredient include glycols such as ethylene glycol, diethylene glycol, triethylene glycol, propylene glycol, polyethylene glycol and polypropylene glycol; fats and oils such as olive oil, castor oil, squalene and lanolin; organic solvents such as dimethyl decyl sulfoxide, methyl octyl sulfoxide, dimethyl sulfoxide, dimethylformamide, dimethylacetamide, dimethyllaurylamide, dodecyl pyrrolidone and isosorbitol; liquid surfactants; plasticizers such as diisopropyl adipate, phthalates and diethyl sebacate; hydrocarbons such as liquid paraffin; ethoxylated stearyl alcohol, glycerol esters, isopropyl myristate, isotridecyl myristate, ethyl laurate, N-methylpyrrolidone, ethyl oleate, oleic acid, isopropyl adipate, isopropyl palmitate, octyl palmitate and 1,3-butanediol. Among the above, phthalic acid esters, isopropyl myristate, isotridecyl myristate and octyl palmitate are preferably used. Either one of these substances or a mixture thereof may be used.

The aforesaid acrylate polymer (ingredient (b)) and the aforesaid liquid ingredient (ingredient (c)) is preferably contained in the crosslinked gel layer at a weight ratio of from 1.0/0.25 to 1.0/2.0, more preferably from 1.0/0.4 to 1.0/2.0 and still preferably from 1.0/0.6 to 1.0/1.8. In contrast, a conventional preparation usually contains a liquid ingredient at a weight ratio less than 1.0/0.25. Such a low content of the liquid ingredient would sometimes make it impossible to achieve a satisfactory low level of the skin irritativeness, from a practical viewpoint.

In the present invention, the ingredients (a) to (c) are blended together and then crosslinked by an appropriate crosslinking procedure so as to give a gel, thus preventing the leakage of the liquid ingredient contained in the preparation and imparting a cohesive power, as described above. Usually, the aforesaid ingredient (b) would undergo the crosslinking reaction. The crosslinking may be effected by a physical means such as irradiation (for example, UV irradiation or electron beam irradiation) or a chemical means with the use of a crosslinking agent (for example, polyisocyanate compound, organic peroxide, organic metal salt, metal alcholate, metal chelate compound, polyfunctional compound).

Among these crosslinking procedures, irradiation or the use of an organic peroxide might sometimes induce decomposition. Further, the use of a highly reactive isocyante or a metal salt or an organic metal salt commonly used in crosslinking reactions might sometimes cause an increase in the viscosity of the solution, which lowers the workability thereof. It is also possible to preliminarily copolymerize a polyfunctional monomer such as diacrylate with the acrylate polymer. In this case, however, there is a possibility that the viscosity of the solution would increase at the polymerization.

In the present invention, therefore, it is preferred to select trifunctional isocyanate or a metal alcholate or a metal chelate compound comprising titanium or aluminum from among the aforesaid crosslinking agents, from the viewpoints of reactivity and handling. These crosslinking agents would not cause any increase in the viscosity of the solution until the completion of the application and drying, which means that they are excellent in workability. When these corsslinking agents are used, the crosslinking reaction can be effected to a certain extent by coating and drying the gel layer, but the coated and dried gel layer is preferably aged at from 40° to 70° C. for stabilizing the properties of the gel layer. The aging time varies depending on the addition amount and the kind of the functional groups of the corssliking agent, and is generally from 2 to 3 days. Such a crosslinking agent is preferably used in an amount of from 0.01 to 2.0 parts by weight per 100 parts by weight of the acrylate copolymer.

The crosslinked gel layer in the present invention contains isosorbide dinitrate as an active ingredient. The content of the isosorbide dinitrate may be appropriately determined depending on the purpose of the administration. It is generally contained in the crosslinked gel layer in an amount of from 2 to 50% by weight, preferably from 10 to 40% by weight. When the content of isosorbide dinitrate is smaller than 2% by weight, the release of a therapeutically effective amount of isosorbide dinitrate cannot be expected. When it exceeds 50% by weight, on the other hand, no improvement in the effect cannot be achieved any more, which brings about an economical disadvantage, and furthermore, the adhesiveness to the skin tends to be deteriorated. When it is required to effect sustained continuous release for a prolonged period of time, to elevate the releasing amount by increasing the content per unit area or to reduce the size of the preparation, however, it is preferred to use the isosorbide dinitrate in an amount exceeding the saturated solubility in the crosslinked gel layer, regardless of the weight ratio range as specified above.

The method for preparing the percutaneous gel preparation according to the present invention is not particularly limited. For example, an ethyl acetate solution of isosorbide dinitrate is added to a solution of an acrylate polymer followed by stirring, and a liquid ingredient is added thereto to form a uniform solution. A crosslinking agent in the form of a solution is added to the above-ontained solution and the viscosity of the resulting solution is adjusted by ethyl acetate to prepare a gel layer coating composition. The coating composition is coated on a separator, and then dried to form a gel layer. The thickness of the gel layer after drying is preferably from 10 to 300 μm, and more preferably from 40 to 150 μm. The resulting gel layer is transferred to a substrate, and then, if necessary, aged at from 40° to 70° C. to obtain a percutaneous gel preparation according to the present invention.

When isosorbide dinitrate is to be added to the crosslinked gel layer, it is preferred that the crosslinked gel layer contains the isosorbide dinitrate as described above. Alternately, it is possible that the isosorbide dinitrate is not contained in the crosslinked gel layer but dissolved in an appropriate solvent and the solution thus-obtained is located at the interface between the crosslinked gel layer and the substrate followed by sealing the periphery of the preparation. When isosorbide dinitrate is separated from the crosslinked gel layer in such a manner as described above, the isosorbide dinitrate can be stably maintained upon storage. In this case, the release of the isosorbide dinitrate can be severely controlled by locating a microporous film between the layer containing the isosorbide dinitrate and the crosslinked gel layer.

The percutaneous gel preparation of the present invention, which has the aforesaid structure, comprises a crosslinked gel layer containing the acrylate polymer and a large amount of the liquid ingredient compatible with the acrylate polymer at a specific ratio. Thus, it is possible to impart a flexibility to the crosslinked gel layer and to reduce the skin irritativeness while maintaining the cohesive powder of the gel layer. When the preparation of the present invention is to be separated from the surface of the skin, therefore, the pain and skin irritativeness caused by the adhesiveness can be reduced. Thus, the percutaneous gel preparation of the present invention has well-balanced adhesiveness to the skin and nonirritativeness.

In the present invention, the standard of the painless removal of the gel preparation from the surface of the skin is specified as follows. In a peeling test with the use of volunteers, namely, the amount of the peeled horny substance caused by the removal of the preparation of the present invention corresponds to 1/5 to ⅔ of those observed in the case of control preparations free from any liquid ingredient. When the amount of the peeled horny substance is outside the above range, either a pain or an insufficient skin-adhesion might be caused.

Further, the preparation of the present invention is in the form of a gel and thus has a high degree of freedom in diffusion and migration of the isosorbide dinitrate, which brings about excellent release of the isosorbide dinitrate.

The present invention will be described in more detail by referring to the following Examples and Comparative Examples, but the present invention is not construed as being limited thereto. In the following Examples and Comparative Examples, all parts and percents are by weight.

EXAMPLE 1

95 Parts of 2-ethylhexyl acrylate and 5 parts of acrylic acid were copolymerized in ethyl acetate under an inert gas atmosphere to thereby give an acrylic copolymer solution.

To 40 parts of the solid content of the above solution, 20 parts of isosorbide dinitrate and 40 parts of isopropyl myristate were added. To 99.8 parts of the above acrylic copolymer, 0.2 parts of aluminum tris(acetylacetonate) which was in the form of a 10% solution in acetylacetone was added. Further, ethyl acetate was added thereto so as to adjust the viscosity of the mixture.

The viscous solution thus-obtained was applied to a polyester separator (thickness: 75 μm) in such a manner as to give a thickness of 40 μm after drying. After drying and crosslinking, a crosslinked gel layer was formed.

The crosslinked gel layer thus-obtained was adhered to the nonwoven fabric face of a laminate film (i.e., a substrate), which was obtained by extruding polyester having a thickness of 2 μm on a polyester nonwoven fabric (12 g/m$^2$). Thus, a percutaneous gel preparation of the present invention was obtained.

EXAMPLE 2

The procedure of Example 1 was repeated except that the thickness of the crosslinked gel layer was changed to 120 μm. Thus, a percutaneous gel preparation of the present invention was obtained.

EXAMPLE 3

The procedure of Example 1 was repeated except that the isopropyl myristate was replaced by octyl palmitate. Thus, a percutaneous gel preparation of the present invention was obtained.

EXAMPLE 4

The procedure of Example 3 was repeated except that the thickness of the crosslinked gel layer was changed to 120 μm. Thus, a percutaneous gel preparation of the present invention was obtained.

EXAMPLE 5

To 30 parts of the solid content of the acrylic copolymer solution obtained in Example 1, 30 parts of isosorbide dinitrate and 40 parts of isotridecyl myristate were added. To 99.7 parts of the above copolymer solution, 0.3 parts of trifunctional isocyanate ("Coronate HL" manufactured by Nippon Polyurethane Co., Ltd.) in the form of a 10% solution in ethyl acetate was added. Further, ethyl acetate was added thereto so as to adjust the viscosity.

The viscous solution thus obtained was dried in the same manner as the one described in Example 1 to thereby give a crosslinked gel layer of 40 μm in thickness. Next, the crosslinked gel layer was adhered to the nonwoven fabric face of the substrate employed in Example 1 to thereby give a percutaneous gel preparation of the present invention.

EXAMPLE 6

The procedure of Example 5 was repeated except that the thickness of the crosslinked gel layer was changed to 120 μm. Thus, a percutaneous gel preparation of the present invention was obtained.

COMPARATIVE EXAMPLE 1

The procedure of Example 1 was repeated except that 20 parts of isosorbide dinitrate was added to 80 parts of the solid content of the acrylic copolymer solution obtained in Example 1 and that ethyl acetate was further added thereto so as to changed the viscosity. Thus, a crosslinked percutaneous preparation free from any liquid ingredient was obtained.

COMPARATIVE EXAMPLE 2

The procedure of Comparative Example 1 was repeated except that the thickness of the crosslinked gel layer was adjusted to 120 μm. Thus, a percutaneous preparation free from any liquid ingredient was obtained.

COMPARATIVE EXAMPLE 3

The procedure of Comparative Example 1 was repeated except that the acrylic copolymer was replaced with a polyisobutyrene rubber polymer comprising 10 parts of polyisobutyrene (viscosity average molecular weight:990,000), 15 parts of polyisobutyrene (viscosity average molecular weight:60,000), 3 parts of polyisobutyrene (viscosity-average molecular weight:1,260) and 7 parts of an alicyclic petroleum resin (softening point:100° C.) while the ethyl acetate was replaced with toluene. Thus, a rubber preparation free from any liquid ingredient was obtained.

COMPARATIVE EXAMPLE 4

The procedure of Comparative Example 1 was repeated except that no crosslinking agent was added. Thus, an uncrosslinked percutaneous preparation free from any liquid ingredient was obtained.

COMPARATIVE EXAMPLE 5

The procedure of Example 1 was repeated except that no crosslinking agent was added. Thus, an uncrosslinked gel preparation containing the liquid ingredient was obtained.

This gel preparation was broken because of low cohesive power. Thus, it could not be subjected to the test which will be described hereinafter.

COMPARATIVE EXAMPLE 6

The procedure of Example 1 was repeated except that 20 parts of isosorbide dinitrate and 15 parts of isopropyl myristate were added to 65 parts of the solid content of the acrylic copolymer solution. Thus, a crosslinked gel preparation containing the liquid ingredient was obtained.

TEST EXAMPLE

Each of the preparations obtained in the above Examples and Comparative Examples was cut into a piece of 50 cm$^2$ (71 mm × 71 mm) and allowed to stand at room temperature for 48 hours. Next, these samples were subjected to the following tests. In the determination of the peeled horny substance, samples comprising a single-layer film (thickness: 9 μm) having no nonwoven fabric laminated as the substrate were employed since the absorption of the dyeing solution by the nonwoven fabric in the substrate might substantially lower the accuracy of the determination.

Tables 1 to 2 show the results.

Rabbit Patch Test

Each of the samples obtained in Examples and Comparative Examples was applied onto the dorsal part of a rabbit from which the hair had been removed. Then, 2 ml portions of the blood of the rabbit were collected after 1.0, 2.5, 4.0, 6.0 and 8.0 hours and the concentration of isosorbide dinitrate in each blood sample was determined by gas chromatography.

Adhesion Test

Each sample in the form of a strip of 12 mm in width was applied to a bakelite plate. Then, a roller of a load of 300 g was moved thereon back and force to thereby secure the adhesion of the sample of the plate. Subsequently, the sample was peeled off in the direction of 180° at a rate of 300 mm/min and the peeling force upon this procedure was measured.

Tack Test

The tack of each sample was evaluated by the probe tack method with the use of a rheometer.

The sample was fixed on a metal plate in such a manner that the face to be adhered to the skin was placed upward. Then, a spherical probe (diameter: 10 mm) was contacted with the sample under a load of 100 g at a rate of 2 cm/min. After maintaining this state for 20 seconds, the spherical probe was separated therefrom at the same rate. The peeling force upon this procedure was measured.

Pain At Peeling

Samples were applied to the inside of upper arms of 5 volunteers. After 30 minutes, the samples were peeled off and the pain thus caused was examined. The pain was evaluated in five grades (1:the least pain) and expressed in the mean of the volunteers. As a standard, the sample prepared in Comparative Example 1 was referred to as 5.

Peeled Horny Substance

Circular samples (diameter:16 mm) were applied to the inside of upper arms of 3 volunteers (A, B and C). After 30 minutes, the samples were peeled off and immersed in a dyeing solution composed of 0.5% of Gentian violet, 0.5% of Brillian green and 98.5% of distilled water for 3 minutes followed by washing with water to thereby dye horny cells.

These samples were then immersed in a 5% aqueous solution of sodium dodecyl sulfate over day and night to thereby extract the dyeing solution. Then, the absorbance of the extract was measured at 595 nm to thereby compare the number of the peeled horny cells. That is, it was considered that a higher absorbance would indicate the larger amount of the peeled horny substance.

A good correlation was observed between the number of the peeled horny cells counted under a stereoscopic microscope and the above-mentioned absorbance.

TABLE 1

| | Rabbit patch test | | |
|---|---|---|---|
| | Maximum blood level (ng/ml) | Time required for achieving maximum blood level (hour) | Area under blood level curve (ng · h/ml) |
| Example 1 | 251 | 2.5 | 1,290 |
| Example 2 | 237 | 2.5 | 1,679 |
| Example 3 | 203 | 2.5 | 1,081 |
| Example 4 | 198 | 2.5 | 1,212 |
| Example 5 | 288 | 2.5 | 1,310 |
| Example 6 | 296 | 2.5 | 1,998 |
| Comparative Example 1 | 122 | 2.5 | 573 |
| Comparative Example 2 | 104 | 2.5 | 552 |
| Comparative Example 3 | 72 | 2.5 | 428 |
| Comparative Example 4 | 126 | 2.5 | 665 |
| Comparative Example 6 | 152 | 2.5 | 744 |

TABLE 2

| | Adhesiveness (g) | Tack (g) | Pain | Peeled horny substance* | | |
|---|---|---|---|---|---|---|
| | | | | A | B | C |
| Example 1 | 122 | 34 | 1.4 | 37.5 | 38.5 | 21.1 |
| Example 2 | 194 | 47 | 1.6 | 40.1 | 35.2 | 28.2 |
| Example 3 | 149 | 37 | 1.4 | 29.2 | 43.1 | 30.4 |
| Example 4 | 202 | 45 | 1.6 | 45.8 | 27.3 | 38.9 |
| Example 5 | 178 | 53 | 1.6 | 31.5 | 42.2 | 40.1 |
| Example 6 | 238 | 60 | 1.4 | 39.1 | 35.4 | 28.3 |
| Comparative Example 1 | 382 | 85 | 5.0 | 121 | 145 | 120 |
| Comparative Example 2 | 518 | 111 | 5.0 | 121 | 115 | 148 |
| Comparative Example 3 | 1,157 | 222 | 4.2 | 130 | 71.2 | 72.2 |
| Comparative Example 4 | 394 | 92 | 3.8 | 100 | 109 | 98.0 |
| Comparative Example 6 | 399 | 92 | 4.2 | 93.0 | 92.0 | 80.0 |

Note: *absorbance of the extract ($\times 10^{-2}$)

As the above Tables 1 and 2 clearly shows, the percutaneous gel preparations according to the present invention show less pain at the peeling and, suffer from the peeling of a smaller amount of the horny substance, compared with the products of Comparative Examples, and furthermore, a large amount of the isosorbide dinitrate would be rapidly absorbed percutaneously.

While the invention has been described in detail and with reference to specific examples thereof, it will be apparent to one skilled in the art that various changes and modifications can be made therein without departing from the spirit and scope thereof.

What is claimed is:

1. A percutaneous gel preparation comprising a substrate having on one surface thereof a crosslinked gel layer formed by crosslinking a composition comprising the following ingredients (a) to (c), the weight ratio of said ingredient (b) to said ingredient (c) being from 1.0/0.25 to 1.0/2.0:
   (a) isosorbide dinitrate;
   (b) an acrylate polymer obtained by polymerizing alkyl (meth)acrylates used in the production of adhesives; and
   (c) a non-aqueous liquid ingredient compatible with said ingredient (b), wherein said ingredient (c) is selected from the group consisting of phthalic acid esters, isopropyl myristate, isotridecyl myristate, and octyl palmitate.

2. A percutaneous gel preparation as claimed in claim 1, wherein said ingredient (b) is an acrylic copolymer obtained by copolymerizing an alkyl (meth)acrylate with (meth)acrylic acid.

3. A percutaneous gel preparation as claimed in claim 1, wherein the weight ratio of said ingredient (b) to said ingredient (c) is from 1.0/0.4 to 1.0/2.0.

4. A percutaneous gel preparation as claimed in claim 3, wherein the weight ratio of said ingredient (b) to said ingredient (c) is from 1.0/0.6 to 1.0/1.8.

5. A percutaneous gel preparation as claimed in claim 1, wherein the content of said isosorbide dinitrate is from 2 to 50% by weight based on the total amount of said crosslinked gel layer.

6. A percutaneous gel preparation as claimed in claim 5, wherein the content of said isosorbide dinitrate is from 10 to 40% by weight based on the total amount of said crosslinked gel layer.

7. A percutaneous gel preparation as claimed in claim 1, wherein said composition further comprises a crosslinking agent selected from a trifunctional isocyanate, a metal alcholate, and a metal chelate compound comprising titanium or aluminum in an amount of from 0.01 to 2.0 parts by weight per 100 parts by weight of said acrylate polymer.

8. A percutaneous gel preparation as claimed in claim 1, wherein the thickness of said crosslinked gel layer is from 10 to 300 μm.

9. A percutaneous gel preparation as claimed in claim 8, wherein the thickness of said crosslinked gel layer is from 40 to 150 μm.

10. A process for producing a percutaneous gel preparation, comprising the following steps:
   (1) providing a composition comprising the following ingredients (a) to (c), the weight ratio of said ingredient (b) to said ingredient (c) being from 1.0/0.25 to 1.0/2.0:
      (a) isosorbide dinitrate;
      (b) an acrylate polymer obtained by polymerizing alkyl (meth)acrylates; and
      (c) a non-aqueous liquid ingredient compatible with said ingredient (b), wherein said ingredient (c) is selected from the group consisting of phthalic acid esters, isopropyl myristate, isotridecyl myristate, and octyl palmitate;
   (2) crosslinking the composition of said step (1) to produce a gel layer; and
   (3) applying said gel layer to a substrate.

* * * * *